United States Patent [19]

Lunetta

[11] Patent Number: 5,164,495
[45] Date of Patent: Nov. 17, 1992

[54] METHOD FOR PREPARING A DICARBOXYLIC ACID HALF-ACID ESTER OF FK506

[75] Inventor: Steven E. Lunetta, Waukegan, Ill.

[73] Assignee: Abbott Laboratories, Abbott Park, Ill.

[21] Appl. No.: 762,097

[22] Filed: Sep. 18, 1991

[51] Int. Cl.⁵ ............... C07D 498/16; A61K 31/395; A61K 31/695
[52] U.S. Cl. .................................... 540/456
[58] Field of Search ......................... 540/456

[56] References Cited

U.S. PATENT DOCUMENTS

| | | | |
|---|---|---|---|
| 4,894,366 | 1/1990 | Okuhara et al. | 540/456 |
| 4,929,611 | 5/1990 | Okuhara et al. | 540/456 |

FOREIGN PATENT DOCUMENTS

| | | | |
|---|---|---|---|
| 0293892A2 | 6/1988 | European Pat. Off. | 540/456 |
| 0379342A2 | 1/1990 | European Pat. Off. | 540/456 |

*Primary Examiner*—Robert T. Bond
*Attorney, Agent, or Firm*—Thomas M. Breininger

[57] ABSTRACT

Disclosed is an improved method for the synthesis of FK506-hemisuccinate for utilization in the preparation of components for as assay for FK506.

9 Claims, No Drawings

METHOD FOR PREPARING A DICARBOXYLIC ACID HALF-ACID ESTER OF FK506

BACKGROUND OF THE INVENTION

1. Technical Field

The present invention is directed to an improved method of making starting materials involved in the preparation of an assay for determining the presence and/or amount of the immunosuppressant drug, FK506, in human blood. More specifically the present invention is directed to the preparation of reaction products of FK506 with dicarboxylic acids or anhydrides thereof.

2. Background

FK506 is an immunosuppressant useful for the treatment of rejection following transplant surgery, graft versus host disease and autoimmune diseases in humans. FK506 is a macrolide antibiotic isolated from the fungus *Streptomyces tsukubaensis* by the Fujisawa Pharmaceutical Company of Japan. Cyclosporine, another immunosuppressant (but having a totally different structure from FK506), has also been used to control rejection. During cyclosporine therapy, monitoring the blood concentration of cyclosporine is an important aspect of clinical care. Accordingly, it is expected that monitoring blood concentrations of FK506 will be important for patients receiving this drug.

To accurately and precisely measure blood concentrations of FK506, an appropriate analytical method must be available. High performance liquid chromatography (HPLC) is one non-immunological method that could be utilized. A receptor based assay could be configured using FK-binding protein and any number of reagents to generate a signal. Numerous immunological configurations can also be envisioned which could be successfully applied to the measurement of FK506.

EP 0 293 892 A2 describes an ELISA methodology to measure FK506 comprised of 1) an ELISA plate coated with anti-FK506 antibodies, 2) an FK506-horseradish peroxidase conjugate which competes with free FK506 and acts as a signal generating reagent and 3) an appropriate substrate for the peroxidase. EP 0 293 892 A2 teaches that an immunogen generally is utilized in the form of a conjugate of FK506 with a carrier such as bovine serum albumin (BSA) by converting the FK506 to a half ester of a dicarboxylic acid such as succinic acid, then reacting the half ester with N-hydroxysuccinimide or the like in the presence of a condensing agent such as dicyclohexylcarbodiimide and further reacting the resulting activated ester with BSA. Pages 6 and 7 of the publication disclose the preparation of the FK506 hemisuccinate utilizing pyridine. However, it has been found that utilization of pyridine tends to result in the formation of disadvantageously low amounts of the product, FK506 half-ester. This tendency has been found, for example, when succinic anhydride has been utilized as the dicarboxylic acid. The achievement of consistently reliable and repeatable yields of reasonable amounts of FK506 half-ester product clearly is desirable. Moreover, the method disclosed in EP 0 293 892 results in undesirable amounts of FK506 being converted into side products thereby reducing the amount of unreacted FK506 that can be recovered following reaction.

The production of low yields of FK506 hemisuccinate coupled with the undesirable amount of side reaction products of FK506 is economically disadvantageous when amounts of FK506 hemisuccinate necessary for commercial scale production are contemplated. Accordingly, an object of the present invention is to provide an improved method for producing esters of FK506 and dicarboxylic acids which reliably will yield improved amounts of the product half-esters of FK506 and, at the same time, reduce the amount of FK506 converted into undesirable side products.

SUMMARY OF THE INVENTION

The invention provides for a method for making a half-ester of FK506 and a dicarboxylic acid (or an anhydride thereof) by reacting a mixture comprising FK506 and the dicarboxylic acid (or anhydride) in the presence of triethylamine. The method of the invention reliably provides for a higher yield of the FK506 half-ester product while minimizing the amount of FK506 converted into undesirable side products.

Reaction products of the invention can be utilized in the preparation of components for diagnostic assays for determining the presence and/or amount of FK506 in biological fluids such as from patient samples.

DETAILED DESCRIPTION OF THE INVENTION

FK506 corresponding to the following structural formula, (I):

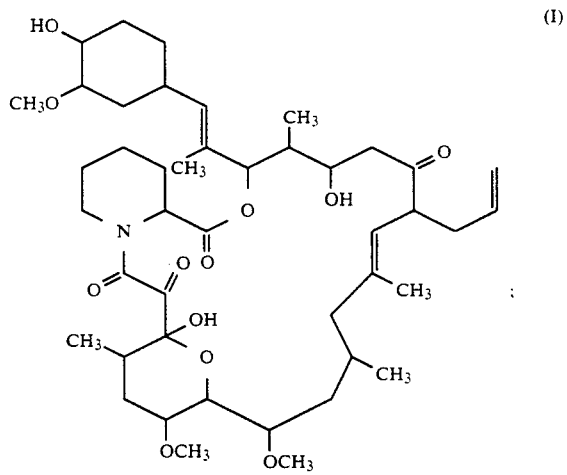

FK506 generally is theoretically considered to be difunctional in hydroxyl groups (not trifunctional) given the presence of a "masked ketone" moiety in the structural formula. Carboxylic acids suitable for the method of the invention are difunctional in carboxyl-(COOH) groups. However, the relative amounts of FK506 and dicarboxylic acid are chosen and reaction conditions are utilized such that on average one dicarboxylic acid molecule reacts with one FK506 molecule with the consequent formation of one FK506 half-ester molecule.

It is to be understood that carboxylic acid anhydrides can be utilized in the method of the invention, and typically are preferred. The acid anhydride of a dicarboxylic acid of course is to be considered difunctional in carboxyl groups. The reaction product of the method of the invention sometimes is referred to herein as a "dicarboxylic acid/FK506 half-ester" or simply as an "FK506 half-ester".

The method for making a half-ester of FK506 and a dicarboxylic acid involves reacting a mixture comprising FK506 and a dicarboxylic acid or anhydride thereof in the presence of triethylamine. It has been found that reacting FK506 with a dicarboxylic acid or anhydride in the presence of triethylamine provides a reliably higher yield of the dicarboxylic acid/FK506 half-ester reaction product than reaction in, for example, pyridine as taught in EP 0 293 892 A2 Moreover, the resulting product formed from the method of the invention typically contains less undesirable side products. For example, one undesirable side product minimized by the method of the invention is believed to be one involving extraction of a hydrogen atom of a methylene group followed by elimination of a hydroxyl group on the neighboring carbon atom in that part of the FK506 molecule represented by the following partial structural formula (II) with consequent formation of an olefinic bond shown in the following structural formula (III).

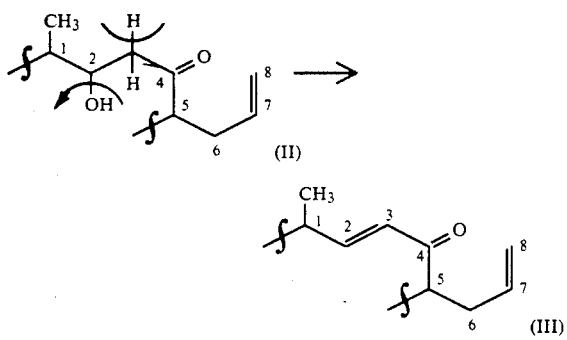

Dicarboxylic acids and anhydrides for the method of the invention generally are of relatively low molecular weight, i.e., having a molecular weight in the range of from 90 to 250, preferably in the range of from 100 to 200. Examples of dicarboxylic acids and anhydrides include: oxalic acid, adipic acid, glutaric acid, maleic acid, maleic anhydride, fumaric acid, succinic acid, succinic anhydride, terephthalic acid, terephthalic anhydride, hexahydroterephthalic acid and hexahydrophthalic anhydride, with succinic anhydride being preferred.

The reaction of the dicarboxylic acid or anhydride with FK506 is carried out in a temperature range of from 5 to 30 degrees Celsius, preferably from 20 to 25 degrees Celsius, for a period of about 12 hours or longer in the presence of triethylamine. Preferably the reaction is carried out at atmospheric temperature and pressure.

Typically, the reaction is carried out by first mixing the dicarboxylic acid or anhydride with FK506 and a catalyst such as dimethylaminopyridine in a solvent such as freshly distilled methylene chloride. Thereafter the triethylamine is added while mixing (stirring) the aforesaid components of the reaction mixture.

The amount of dicarboxylic acid or anhydride for the preparation of the FK506 half-ester may vary. However, typically an amount is chosen to provide a ratio of five moles of dicarboxylic acid (or anhydride) to one mole of FK506 so as to provide a molar excess of the acid or anhydride.

The amount of FK506 and the amount of triethylamine are selected to provide a ratio of about 1.0 mole of FK506 to about 1 mole of triethylamine, preferably 1.0:1.0.

A dicarboxylic acid/FK506 half-ester of the invention is particularly useful as an intermediate in the preparation of various conjugates for utilization in diagnostic assays for FK506. For example, the FK506 half-esters of the invention have been found to be particularly useful as intermediates in the conjugation of FK506 to an enzyme such as alkaline phosphatase. Other enzymes such as peroxidase, $\beta$-D-galactosidase, glucose oxidase, acetylcholine esterase, glucose-6-phosphate dehydrogenase, malate dehydrogenase and urease may also be utilized. Also by way of example the FK506 half-esters of the invention can also be utilized as intermediates in the conjugation of FK506 to various poly(amino) acids in the preparation of immunogens for raising antibodies. Examples of such poly(amino)acids include: naturally occuring poly(amino) acids such as bovine serum albumin (BSA), keyhole limpet hemocyanin (KLH), egg ovalbumin, bovine gamma globulin (BGG), thyroxine binding globulin, etc., and synthetic poly(amino-acids) such as polylysine, etc.

Dicarboxylic acid/FK506 half-esters of the invention have been found to be especially useful in the preparation of preferred covalent conjugates of FK506 and alkaline phosphatase for utilization in a microparticle capture enzyme immunoassay (MEIA) for FK506 run on the IMx ® analyzer available from Abbott Laboratories. Such an assay is illustrated more specifically in the examples which follow. A general description of microparticle capture enzyme immunoassays can be found in "*The Abbott IMx TM Automated Benchtop Immunochemistry Analyzer System*", by M. Fiore et al in *CLINICAL CHEMISTRY* Vol. 34, No. 9, 1726–1732 (1988) the disclosure of which is hereby incorporated by reference.

In general an analyte such as FK506 is determined in an MEIA by quantifying the rate of fluorescence development when a fluorogenic substrate is converted by the action of an enzyme-labeled conjugate. MEIAs as run on the IMx ® analyzer generally utilize a reagent pack containing microparticle reagent, an alkaline phosphatase conjugate, fluorogenic substrate and, optionally, a diluent buffer specific for the FK506 assay. Submicron microparticles coated with a capture molecule specific for FK506 being measured are used as the solid phase. Because the microparticles do not settle out of suspension during the course of the assay, they can be readily pipetted by the IMx ® instrument. The effective surface area of these polystyrene latex microparticles, which number in the millions, is several-fold greater than that of a ¼ inch diameter polystyrene bead commonly used in other commercial immunoassays. Because of this large surface area and the very small diffusion distance between analyte and the capture molecules on the surface of the microparticles, the capture phase of the MEIA typically reaches equilibrium within several minutes, allowing excellent throughput.

Unlike homogeneous fluorescent polarization immunoassays, the heterogeneous MEIA requires a separation step. After incubation of the microparticles with specimen, the microparticles are separated from the reaction mixture by transferring it to an inert glass fiber matrix in the MEIA reaction cell. This glass fiber surface provides a precisely located mechanical support for the microparticles during the subsequent optical read phase of the assay. The microparticles and bound analyte adhere strongly to the glass fibers, while the remaining specimen components are washed through the pores of the matrix to an underlying absorbent blotter. Detection of the immune complex on the glass fiber matrix is accomplished using an alkaline phosphatase-labeled conjugate. Conjugate is either incubated with the specimen and microparticles in a typical one step IMx® MEIA or applied to the matrix after the initial wash step. It is contemplated that an MEIA for FK506 run on the IMx® analyzer can be configured either in a "sandwich" or competitive assay format. In a sandwich configuration an alkaline phosphatase-anti-FK506 antibody conjugate is used, while an IMx® competitive assay utilizes an FK-506-alkaline phosphatase conjugate.

In either configuration, the specifically bound alkaline phosphatase on the microparticles is detected by addition of a fluorogenic substrate, typically 4-methylumbelliferyl phosphate (4-MUP), to the matrix. The alkaline phosphatase catalyzes hydrolysis of the 4-MUP to inorganic phosphate and fluorescent 4-methylumbelliferone (4-MU). The liberated 4-MU is detected by the IMx® MEIA optics assembly, a front surface fluorometer designed to detect fluorescence of low concentrations of 4-MU without interference by fluorescence of 4-MUP at 367 nanometers (nm). A system of lenses and optical filters focuses filtered light (365 nm wavelength) from a mercury arc lamp onto the surface of the matrix and focuses emitted fluorescence from 4-MU (448 nm wavelength) onto a photomultiplier tube. About 5% of the excitation light is detected by a photodiode, allowing normalization of the fluorescence data and generation of a control signal used by the lamp power supply to maintain the intensity of the excitation light within 5% over the useful life of the lamp. The instrument then uses linear regression analysis to convert the data from 8 successive determinations of 4-MU fluorescence to a rate, which rate is proportional to the concentration of alkaline phosphatase conjugate specifically bound to the microparticles, from which the concentration of FK506 in the sample can be determined.

The following examples are provided to further illustrate embodiments of the invention and should not be construed as a limitation on the scope of the invention.

EXAMPLE 1

This example illustrates the preparation of polyclonal antibodies directed against FK506.

Rabbitt polyclonal antibodies were produced by standard procedures. FK506 immunogen was prepared as described in Fujisawa patent EP 0 293 892 A2 the disclosure of which is specifically incorporated herein by reference.

EXAMPLE 2

This example illustrates the preparation of Microparticle Reagent.

An antibody directed against FK506 was covalently coupled to carboxylate modified latex microparticles (0.392 microns) by established procedures. These methods are extensively reviewed in Uniform Latex Particles (1987) L. B. Bangs, Seragen Diagnostics, Inc., the disclosure of which is hereby specifically incorporated by reference. In brief, final concentrations of antibody (1 to 3 mg/ml), microparticles (0.5 to 0.7% solids) and EDAC (1-ethyl-3-(3-dimethylaminopropyl)carbodiimide hydrochloride) (0.2–0.5 mM) are mixed, the pH adjusted to 5.7 and the reaction allowed to proceed for 12–18 hours at 2–8 degrees Celsius. The microparticles are then washed by repetitive centrifugation and re-suspension cycles and the microparticles are diluted to the final working concentration. These methods are applicable to either polyclonal or monoclonal antibodies.

Microparticles were prepared using both polyclonal antibodies and a monoclonal antibody produced by Fujisawa (clone 1-60-46, described in Trans Proc, Vol 9, No 5, Suppl. 6, pp 23-29, 1987), the disclosure of which is specifically incorporated herein by reference.

EXAMPLE 3

This example illustrates the preparation of FK506-hemisuccinate and its active ester according to the method of the invention.

FK506 (250 mg), succinic anhydride (150 mg) and 4-dimethylaminopyridine (61 mg) were dissolved in 6.25 ml of freshly distilled methylene chloride. Upon stirring, triethylamine (4.2 microliters) was added and the reaction mixture was stirred for an additional 20 hours at room temperature. The mixture was diluted to 20 ml with methylene chloride and washed once with 0.1N aqueous HCl, once with distilled water and once with saturated aqueous NaCl. The resulting organic phase was dried over anhydrous $MgSO_4$, filtered and concentrated to a slightly yellow foam. This material was chromatographed on silica gel using a 9:1 methylene chloride/methanol mobile phase to give 104.3 mg (39% yield) of the hemisuccinate as a white foam.

The FK506 hemisuccinate (35 mg), N-hydroxysuccinimide (5.4 mg) and N,N'-dicyclohexylcarbodiimide (8.8 mg/ml) were dissolved in 5 ml ethyl acetate and stirred for 24 hours at room temperature. The reaction mixture was filtered and dried to give 44.1 mg of a mixture containing the active ester and N,N'-dicyclohexylurea. The material was used without further purification.

EXAMPLE 4

This example illustrates the preparation of the FK506-Alkaline Phosphate Conjugate Reagent.

One milligram (1 mg) of the active ester described above was solubilized in 0.5 ml of dimethylformamide (DMF). An amount of 0.14 ml of this solution was mixed with 0.62 ml of DMF and added to 10 ml of calf intestine alkaline phosphatase (10 mg). The solution was mixed for 2.5 hours at room temperature and then 1 ml of 1.8M Tris was added. This solution was dialyzed against buffer (0.1M NaCl, 2 mM $MgCl_2$, 0.1 mM $ZnCl_2$, 0.1% $NaN_3$, 0.05M Tris-HCl, pH=7.5) at 2–8 degrees Celsius and then bovine serum albumin was added to a final concentration of 1%. This stock solution of FK506-alkaline phosphatase conjugate was diluted to the working concentrations as necessary.

EXAMPLE 5

This example illustrates the preparation of Precipitation Reagent.

The whole blood precipitation reagent was prepared with final concentrations of 60 mM $ZnSO_4$, 50% (w/v) methanol and 30% ethylene glycol.

EXAMPLE 6

This example illustrates the preparation of Blood FK506 Standards.

Human whole blood was lyzed by three freeze-thaw cycles and the pH of the blood adjusted to pH 6.0 by the addition of 3M citric acid. FK506 in methanol (10 micrograms/ml) was spiked into this matrix so as to make standards from 10 to 80 nanograms/ml of FK506. This novel matrix for FK506 is described in the copending U.S. patent application Ser. No. 07/752410 filed Aug. 30, 1991 of Frank C. Grenier, Julie A. Luczkiw, Merry E. Bergmann and David R. Blonski and entitled "Stable Aqueous FK506 Standards", the disclosure of which is specifically incorporated herein by reference.

EXAMPLE 7

This example illustrates a Microparticle Enzyme Immunoassay (MEIA) for FK506.

Whole blood solutions containing 0, 10, 20, 30, 50 and 80 nanograms/ml FK506 were each tested following the assay protocol described below. One hundred (100) microliters of sample was added to 200 microliters of precipitation reagent and the mixture vortexed for 5-10 seconds. The precipitates formed were pelleted by centrifugation and the clear supernatant decanted into the sample well of an IMx ® sample cartridge. Forty (40) to 50 microliters of this organic sample was added directly to 50 microliters of the microparticle reagent and 150-160 microliters of IMx ® dilution buffer. The reaction mixture was incubated at 33-36 degrees Celsius for 10 minutes and then 175 microliters of this mixture was transferred onto a glass fiber filter. The filter was washed with IMx ® dilution buffer and then 40-50 microliters of the FK506-alkaline phosphatase conjugate reagent was added to the filter. Following a second wash step, 50 microliters of alkaline phosphatase substrate, 4-methylumbelliferyl phosphate was added to the filter. Conjugate bound to the filter converted the substrate to a fluorescent product which was quantified by front surface fluorescence measurements. The rate of production of the product was directly proportional to the amount of conjugate bound and thus indirectly proportional to the amount of FK506 bound to the microparticles. The results of the measurements are as set forth in the following Tables 1 and 2.

TABLE 1

| Using Microparticles with Monoclonal Antibody | |
|---|---|
| Concentration FK506 (ng/ml) | Fluorescent Rate |
| 0 | 416 |
| 10 | 288 |
| 20 | 197 |
| 30 | 150 |
| 50 | 111 |
| 80 | 79 |

TABLE 2

| Using Microparticles with Polyclonal Antibody | |
|---|---|
| Concentration FK506 (ng/ml) | Fluorescent Rate |
| 0 | 413 |
| 5 | 264 |
| 10 | 208 |
| 20 | 154 |
| 40 | 112 |
| 75 | 85 |

The measurements obtained show that a standard curve can be made to analyze whole blood containing unknown FK506 concentrations. Microparticles made with either polyclonal or monoclonal antibodies function equally well.

What is claimed is:

1. A method for making a half-ester of FK506 and a dicarboxylic acid by reacting a mixture comprising FK506 and a dicarboxylic acid or anhydride thereof having a molecular weight in the range of from 90 to 250 in the presence of triethylamine.

2. The method of claim 1 wherein the reaction of said mixture is conducted in a temperature range of from 5 to 30 degrees Celsuis.

3. The method of claim 2 wherein the reaction of said mixture is conducted in a temperature range of from 20 to 25 degrees Celsius.

4. The method of claim 2 wherein the reaction of said mixture is conducted for a time period of at least 12 hours.

5. The method of claim 1 wherein said dicarboxylic acid is selected from the group consisting of oxalic acid, adipic acid, glutaric acid, maleic acid, fumaric acid, succinic acid, terephthalic acid and hexahydroterephthalic acid, or an anhydride thereof.

6. The method of claim 1 wherein said dicarboxylic acid is succinic acid of the anhydride thereof.

7. The method of claim 1 wherein the amount of FK506 and the amount of said dicarboxylic acid are selected to provide a ratio of about 1 mole of said FK506 to about 5 moles of said dicarboxylic acid.

8. The method of claim 1 wherein the amount of FK506 and the amount of triethylamine are selected to provide a ratio of about 1 mole of said FK506 to about 1 mole of said triethylamine.

9. The method of claim 1 wherein the reaction of said mixture is conducted in a temperature range of from 20 to 25 degrees Celsuis, said dicarboxylic acid is succinic acid or the anhydride thereof, and said FK506, said dicarboxylic acid and said triethylamine are reacted in a molar ratio respectively of 1:5:1.

* * * * *